(12) United States Patent
Quinn

(10) Patent No.: US 8,556,961 B2
(45) Date of Patent: Oct. 15, 2013

(54) METHOD OF DEPLOYING A BIFURCATED SIDE-ACCESS INTRAVASCULAR STENT GRAFT

(75) Inventor: Stephen F. Quinn, Eugene, OR (US)

(73) Assignee: W. L. Gore & Associates, Inc., Newark, DE (US)

( * ) Notice: Subject to any disclaimer, the term of this patent is extended or adjusted under 35 U.S.C. 154(b) by 799 days.

(21) Appl. No.: 11/971,426

(22) Filed: Jan. 9, 2008

(65) Prior Publication Data

US 2008/0109066 A1    May 8, 2008

Related U.S. Application Data

(60) Division of application No. 10/277,641, filed on Oct. 22, 2002, now abandoned, which is a continuation-in-part of application No. 09/734,987, filed on Dec. 11, 2000, now Pat. No. 6,645,242.

(51) Int. Cl.
*A61F 2/06*    (2013.01)

(52) U.S. Cl.
USPC .......................... 623/1.35; 623/1.13; 623/903

(58) Field of Classification Search
CPC .................................... A61F 2/04; A61F 2/07
USPC ............. 623/1.13, 1.16, 1.35, 1.3, 1.31, 1.37, 623/1.27
See application file for complete search history.

(56) References Cited

U.S. PATENT DOCUMENTS

| | | | |
|---|---|---|---|
| 5,197,976 A | 3/1993 | Herweck et al. | |
| 5,628,787 A | 5/1997 | Mayer | |
| 5,755,773 A * | 5/1998 | Evans et al. | 606/194 |
| 5,755,778 A | 5/1998 | Kleshinski | |
| 5,788,681 A | 8/1998 | Weaver et al. | |
| 5,824,040 A * | 10/1998 | Cox et al. | 623/1.35 |
| 5,855,598 A | 1/1999 | Pinchuk | |
| 5,893,887 A | 4/1999 | Jayaraman | |
| 5,906,641 A | 5/1999 | Thompson et al. | |
| 5,957,974 A | 9/1999 | Thompson et al. | |
| 5,972,023 A | 10/1999 | Tanner et al. | |
| 5,984,955 A | 11/1999 | Wisselink | |
| 5,993,481 A | 11/1999 | Marcade et al. | |
| 6,048,360 A | 4/2000 | Khosravi et al. | |
| 6,090,136 A | 7/2000 | McDonald et al. | |
| 6,093,203 A | 7/2000 | Uflacker | |

(Continued)

FOREIGN PATENT DOCUMENTS

JP    2000/279532    10/2000

*Primary Examiner* — Brian E. Pellegrino
(74) *Attorney, Agent, or Firm* — Gilbert R. Gabo

(57) ABSTRACT

A bifurcated intravascular stent graft comprises primary stent segments and a primary graft sleeve, forming a main fluid channel and having a side opening therethrough. An external graft channel formed on the primary graft sleeve has a first end communicating with the side opening and an open second end outside the primary graft sleeve, thereby providing a branch flow channel from the main channel out through the side opening and external graft channel. The primary stent segments and graft sleeve engage an endoluminal surface of a main vessel and form substantially fluid-tight seals. The stent graft further comprises a secondary stent graft, which may be positioned partially within the external graft channel, through the open second end thereof, and partially within a branch vessel. The secondary stent graft engages the inner surface of the external graft channel and the endoluminal surface of the branch vessel, thereby forming substantially fluid-tight seals.

5 Claims, 12 Drawing Sheets

(56) References Cited

U.S. PATENT DOCUMENTS

| | | |
|---|---|---|
| 6,129,756 A | 10/2000 | Kugler et al. |
| 6,210,429 B1 | 4/2001 | Vardi et al. |
| 6,334,867 B1 | 1/2002 | Anson |
| 6,344,056 B1 | 2/2002 | Dehdashtian |
| 6,355,056 B1 | 3/2002 | Pinheiro |
| 6,645,242 B1 | 11/2003 | Quinn |
| 6,811,566 B1 * | 11/2004 | Penn et al. ............ 623/1.35 |
| 6,814,752 B1 * | 11/2004 | Chuter ............ 623/1.35 |

* cited by examiner

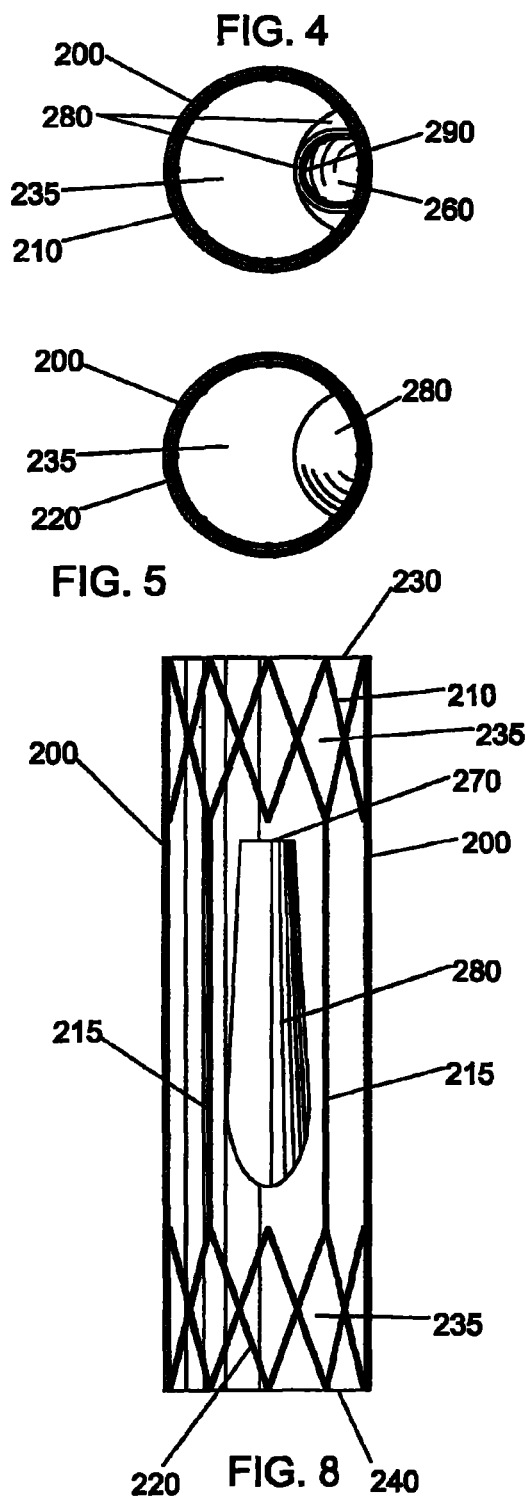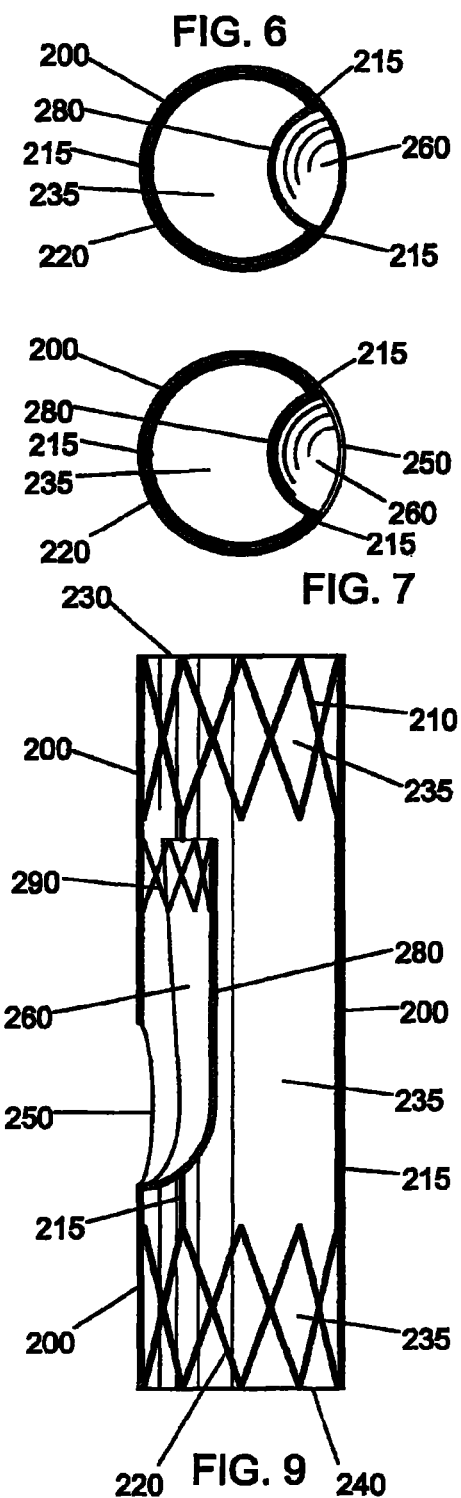

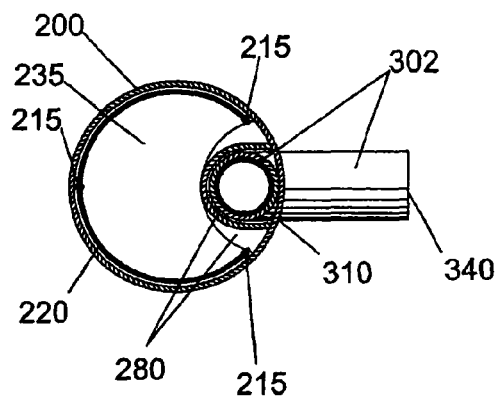
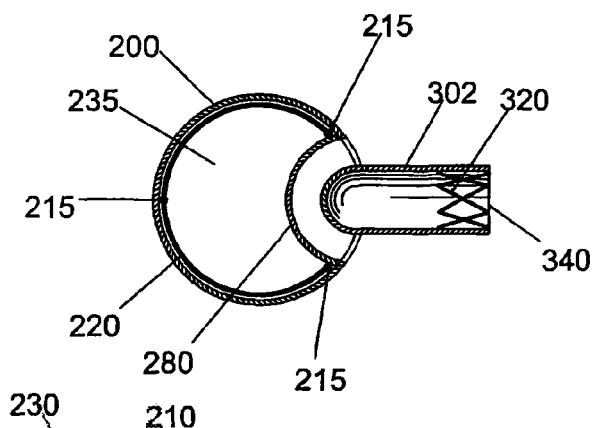
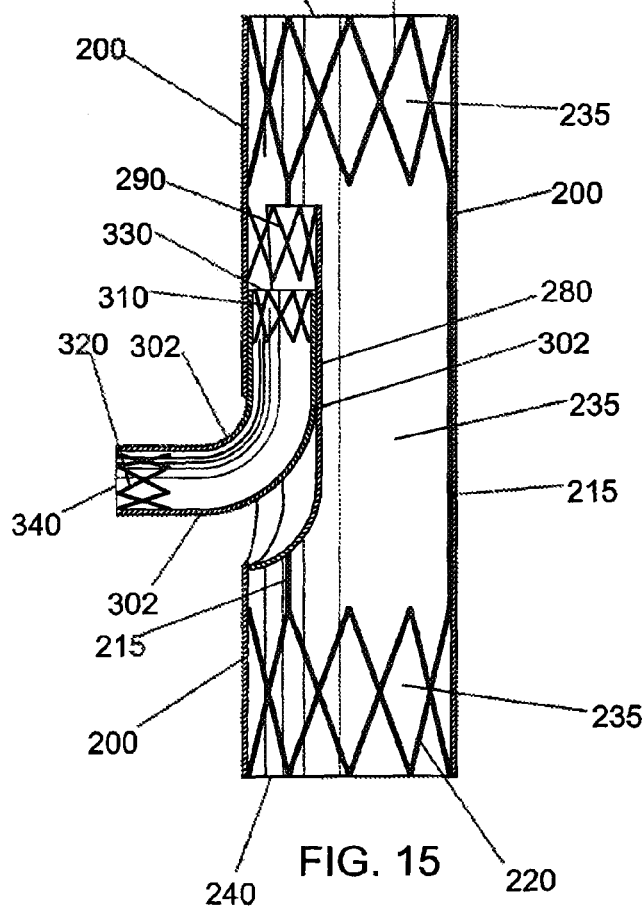

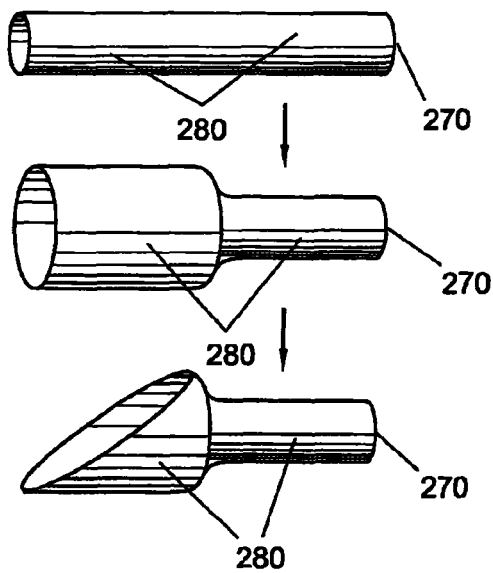
FIG. 23
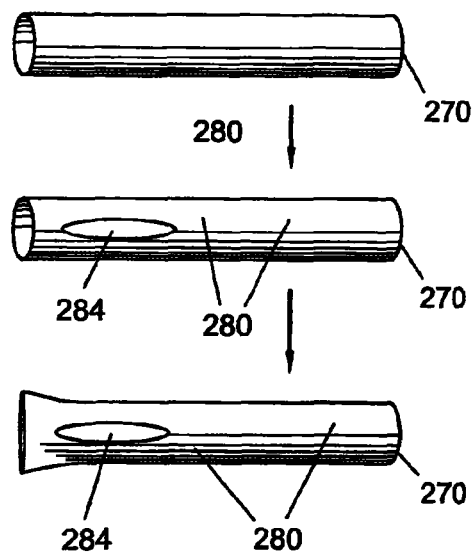
FIG. 25
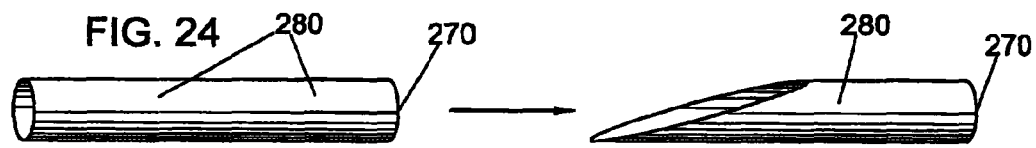
FIG. 24
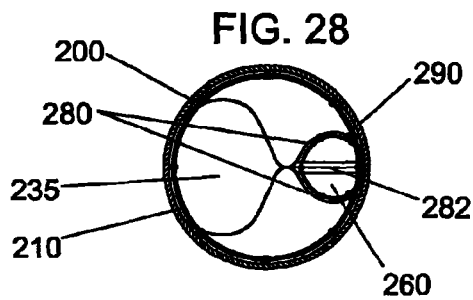
FIG. 28
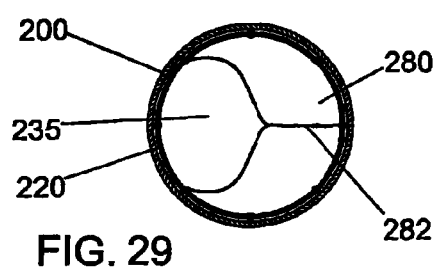
FIG. 29
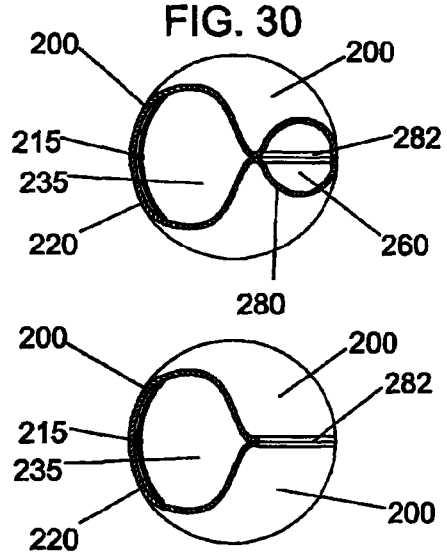
FIG. 30
FIG. 31

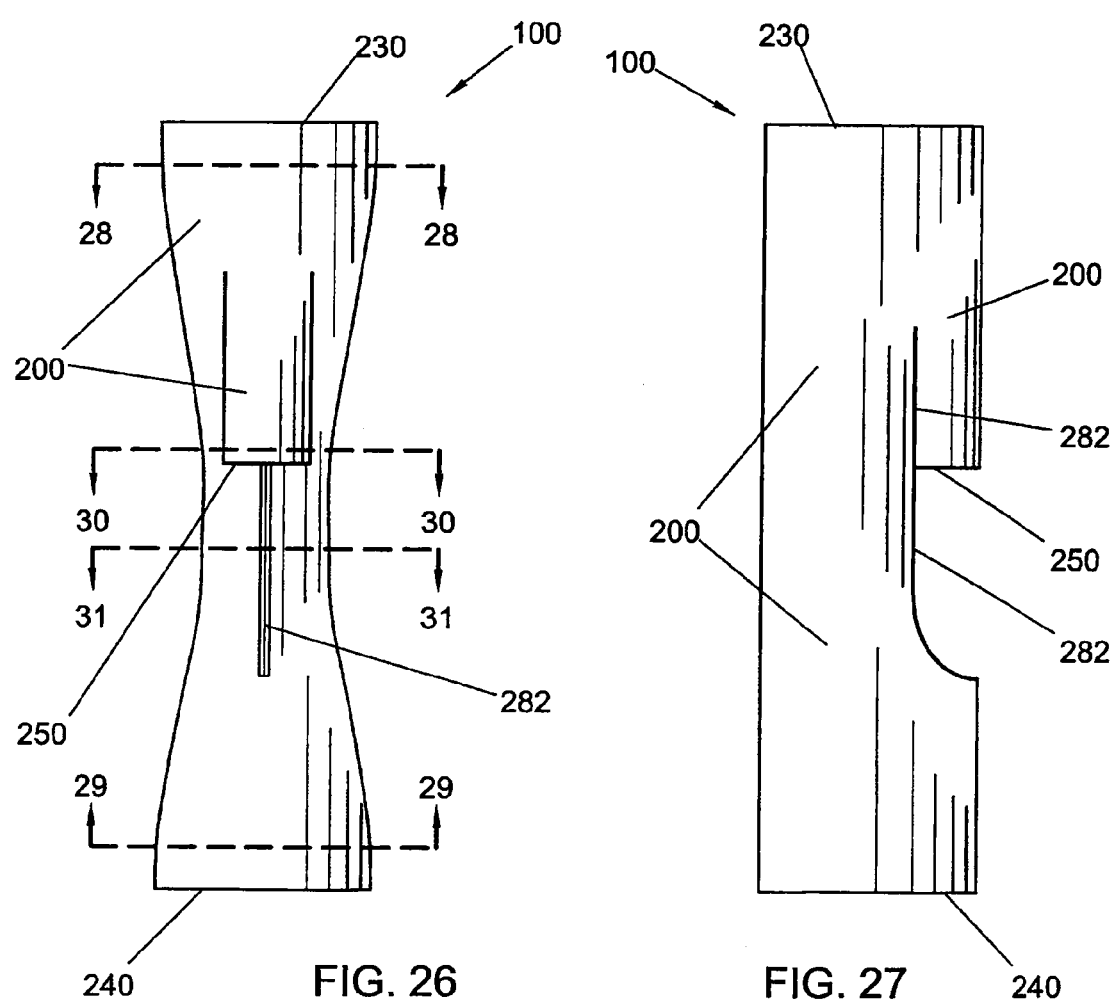

METHOD OF DEPLOYING A BIFURCATED SIDE-ACCESS INTRAVASCULAR STENT GRAFT

CROSS-REFERENCE TO RELATED APPLICATIONS

This application is a division of U.S. application Ser. No. 10/277,641 filed Oct. 22, 2002 now abandoned, which is a continuation-in-part of U.S. application Ser. No. 09/734,987 filed Dec. 11, 2000, now issued U.S. Pat. No. 6,645,242.

FIELD OF THE INVENTION

The field of the present invention relates to intravascular stent grafts. In particular, a bifurcated side-access intravascular stent graft and methods for fabricating and deploying the same are described herein.

BACKGROUND

In many instances of vascular disease, a damaged, weakened, and/or enlarged portion of a blood vessel must be protected from intravascular fluid pressure. Continued exposure to such fluid pressure may result in progression of damage to the affected area and/or vessel failure, accompanied by significant morbidity or even sudden death. A well-established technique for treating such vascular damage is the use of transluminally-deployed stent grafts.

Briefly, a stent graft comprises two major components, a stent and a graft. The stent (one or more) typically takes the form of a somewhat stiff tube-like structure inserted into an affected vessel and fixed in place. The stent may serve to maintain a patent vessel lumen, may serve as structural support for the vessel, and/or may serve as an attachment/seal for a graft. A graft typically takes the form of a flexible tube or sleeve which is at least somewhat fluid-tight (although varying degrees of permeability may be desirable for a variety of reasons). When secured within a vessel using stents (a single stent the length of the graft, a pair of stent segments at the ends of the graft, or multiple stent segments spaced along the length of the graft), the graft becomes a surrogate vessel-within-a-vessel, and bears the brunt of the intravascular fluid pressure. It has become common practice to bridge damaged vessel segment using a sufficiently long graft secured within the vessel with stent segments.

Complications arise, however, when vessel damage occurs near a vessel branch point. More elaborate, multi-component devices are required to both shield the damaged vessel portion while maintaining blood flow through the main and branch vessels. Such devices are described in the following patents and references cited therein. Each of the following patents is hereby incorporated by reference as if fully set forth herein: U.S. Pat. No. 5,906,641; U.S. Pat. No. 6,093,203; U.S. Pat. No. 5,855,598; U.S. Pat. No. 5,972,023; U.S. Pat. No. 6,129,756; U.S. Pat. No. 5,824,040; U.S. Pat. No. 5,628,787; and U.S. Pat. No. 5,957,974.

Many of the prior-art devices are suitable for vessel branches where the branch vessel leaves the main vessel at a relatively small angle (less than about 45°, or example). For larger branching angles (as large as about 90° or even up to about 180°, for example) many prior art devices are not suitable. Such large branching angles occur at several potentially important repair sites (particularly along the abdominal aorta, at the renal arteries, celiac artery, superior and inferior mesenteric arteries, for example). Another drawback common to many devices of the prior-art is the need for transluminal access through the branch vessel from a point distal of the repair site. In many instances such access is either impossible (celiac artery, mesenteric arteries, renal arteries) or extremely difficult and/or dangerous (carotid arteries). Still other previous devices do not provide a substantially fluid-tight seal with the branch vessel, thereby partially defeating the purpose of the stent graft (i.e., shielding the repaired portion of the main vessel and/or branch vessel from intravascular fluid pressure).

It is therefore desirable to provide a bifurcated side-access intravascular stent graft and methods for fabricating and deploying the same, wherein the stent graft may be deployed transluminally to repair vessels having large-angle branch vessels (ranging from about 0° up to about 180°, for example). It is therefore desirable to provide a bifurcated side-access intravascular stent graft and methods for fabricating and deploying the same, providing a substantially fluid-tight seal with the main vessel and the branch vessel. It is therefore desirable to provide a bifurcated side-access intravascular stent graft and methods for fabricating and deploying the same, wherein the stent graft may be deployed transluminally without distal access through the branch vessel. It is therefore desirable to provide a bifurcated side-access intravascular stent graft and methods for fabricating and deploying the same, wherein the stent graft may be readily and accurately positioned relative to the branch vessel.

SUMMARY OF THE INVENTION

Certain aspects of the present invention may overcome one or more aforementioned drawbacks of the previous art and/or advance the state-of-the-art of bifurcated intravascular stent graft and methods for fabricating and deploying the same, and in addition may meet one or more of the following objects:

To provide a bifurcated intravascular stent graft and methods for fabricating and deploying the same, wherein the stent graft may be deployed transluminally to repair vessels having large-angle branch vessels (ranging from about 0° up to about 180°);

To provide a bifurcated intravascular stent graft and methods for fabricating and deploying the same, providing a substantially fluid-tight seal with the main vessel and the branch vessel;

To provide a bifurcated intravascular stent graft and methods for fabricating and deploying the same, wherein the stent graft may be deployed transluminally without distal access within the branch vessel;

To provide a bifurcated intravascular stent graft and methods for fabricating and deploying the same, wherein the stent graft may be readily and accurately positioned relative to the branch vessel;

To provide a bifurcated intravascular stent graft and methods for fabricating and deploying the same, wherein a primary stent graft is provided with a side opening;

To provide a bifurcated intravascular stent graft and methods for fabricating and deploying the same, wherein a primary stent graft is provided with an external primary graft channel communicating with the side opening;

To provide a bifurcated intravascular stent graft and methods for fabricating and deploying the same, wherein the primary stent graft may be provided near each end thereof with a stent segment;

To provide a bifurcated intravascular stent graft and methods for fabricating and deploying the same, wherein the external primary graft channel may be provided with a stent segment;

To provide a bifurcated intravascular stent graft and methods for fabricating and deploying the same, wherein a primary stent graft may be deployed within a main vessel with the side opening substantially aligned with a branch vessel;

To provide a bifurcated intravascular stent graft and methods for fabricating and deploying the same, wherein a secondary stent graft may be deployed within the external graft channel and within the branch vessel; and To provide a bifurcated intravascular stent graft and methods for fabricating and deploying the same, wherein the secondary stent graft may be provided near each end thereof with a stent segment.

One or more of the foregoing objects may be achieved in the present invention by a bifurcated side-access intravascular stent graft, comprising: a) first and second primary stent segments; b) a primary graft sleeve operatively coupled near the open ends thereof to the stent segments, forming a main fluid flow channel, and having a side opening therethrough; and c) an external graft channel formed on the primary graft sleeve. The external graft channel has an inner open end communicating with the side opening of the primary graft sleeve and an outer open end, thereby forming a branch fluid flow channel from the main fluid flow channel through the side opening of the primary graft sleeve. The primary stent segments and corresponding open ends of the primary graft sleeve are adapted for engaging an endoluminal surface of a main vessel and forming substantially fluid-tight seals therewith. The primary stent graft may be delivered transluminally to a repair site of the main vessel, rotated to substantially align the outer opening of the external graft channel with a branch vessel, and the primary stent segments engaged with the endoluminal surface of the main vessel, thereby forming substantially fluid-tight seals therewith.

The bifurcated intravascular stent graft may further comprise a secondary stent graft comprising first and second secondary stent segments and a secondary graft sleeve operatively coupled to the secondary stent segments near its open ends. The secondary stent graft is adapted for passing into the external graft channel through the side opening of the primary graft sleeve, through the external graft sleeve, and into a branch vessel. The secondary stent graft may be delivered transluminally and inserted through the side opening and into the external graft channel, while remaining at least partially within the external graft channel. The secondary stent segments may then be engaged with the inner surface of the external graft channel and the endoluminal surface of the branch vessel, thereby forming substantially fluid-tight seals therewith.

Additional objects and advantages of the present invention may become apparent upon referring to the preferred and alternative embodiments of the present invention as illustrated in the drawings and described in the following written description and/or claims.

BRIEF DESCRIPTION OF THE DRAWINGS

FIG. 4 shows a transverse-sectional view of a primary stent graft according to the present invention.

FIG. 5 shows a transverse-sectional view of a primary stent graft according to the present invention.

FIG. 6 shows a transverse-sectional view of a primary stent graft according to the present invention.

FIG. 7 shows a transverse-sectional view of a primary stent graft according to the present invention.

FIG. 8 shows a longitudinal-sectional view of a primary stent graft according to the present invention.

FIG. 9 shows a longitudinal-sectional view of a primary stent graft according to the present invention.

FIG. 13 shows a transverse-sectional view of a bifurcated stent graft according to the present invention.

FIG. 14 shows a transverse-sectional view of a bifurcated stent graft according to the present invention.

FIG. 15 shows a longitudinal-sectional view of a bifurcated stent graft according to the present invention.

FIG. 23 shows a procedure for adapting an internal graft sleeve according to the present invention.

FIG. 24 shows a procedure for adapting an internal graft sleeve according to the present invention.

FIG. 25 shows a transverse-sectional view of a primary stent graft according to the present invention.

FIG. 26 shows a front view of a bifurcated stent graft according to the present invention.

FIG. 27 shows a side view of a bifurcated stent graft according to the present invention.

FIG. 28 shows a transverse-sectional view of a bifurcated stent graft according to the present invention.

FIG. 29 shows a transverse-sectional view of a bifurcated stent graft according to the present invention.

FIG. 30 shows a transverse-sectional view of a bifurcated stent graft according to the present invention.

FIG. 31 shows a transverse-sectional view of a bifurcated stent graft according to the present invention.

Figure 1:
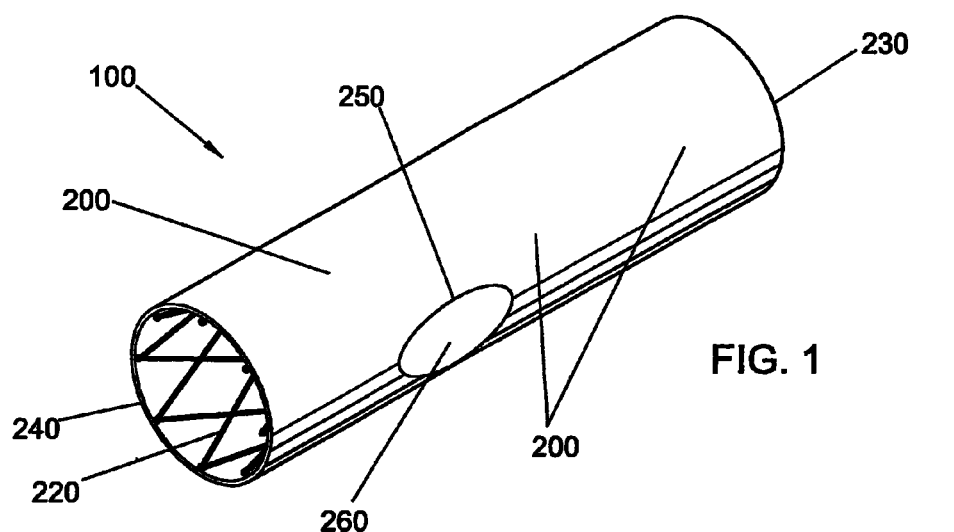
FIG. 1 shows an isometric view of a primary stent graft according to the present invention.
Figures 2, 3:
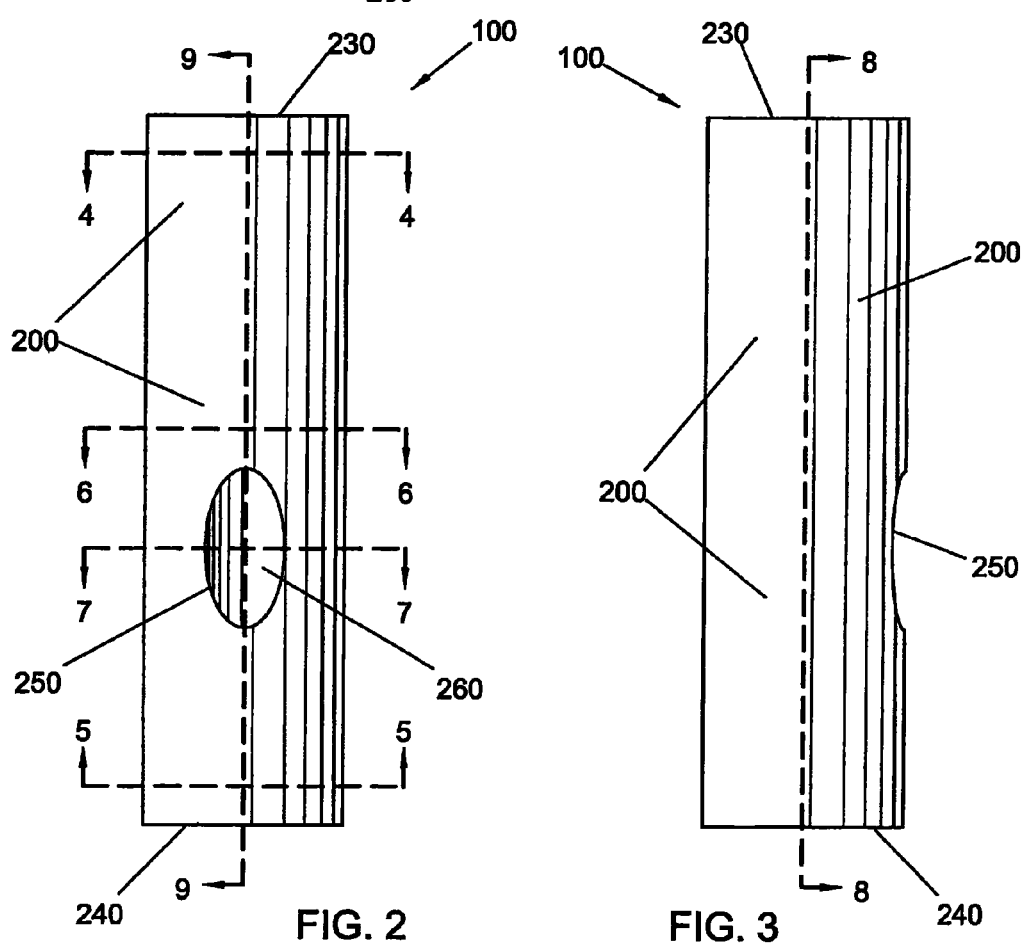
FIG. 2 shows a front view of a primary stent graft according to the present invention.
FIG. 3 shows a side view of a primary stent graft according to the present invention.
Figure 10:
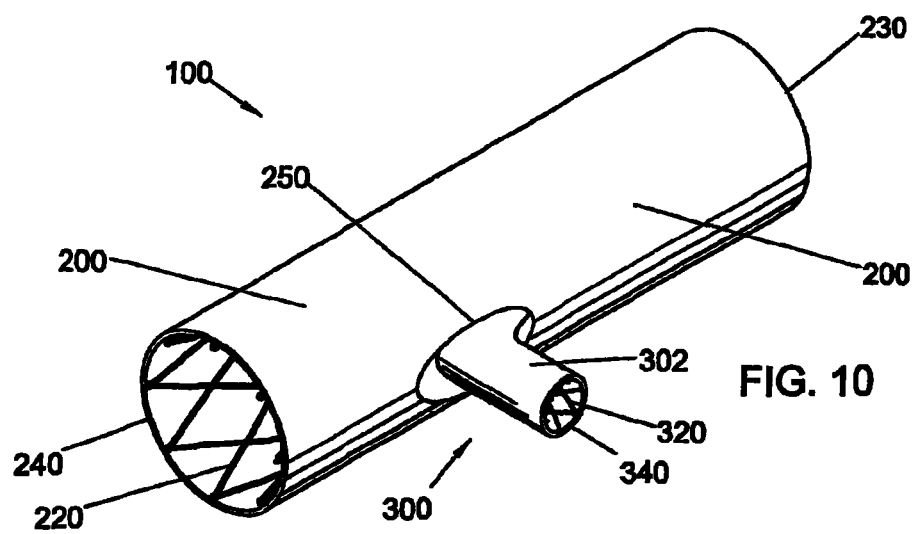
FIG. 10 shows an isometric view of a bifurcated stent graft according to the present invention.
Figures 11, 12:
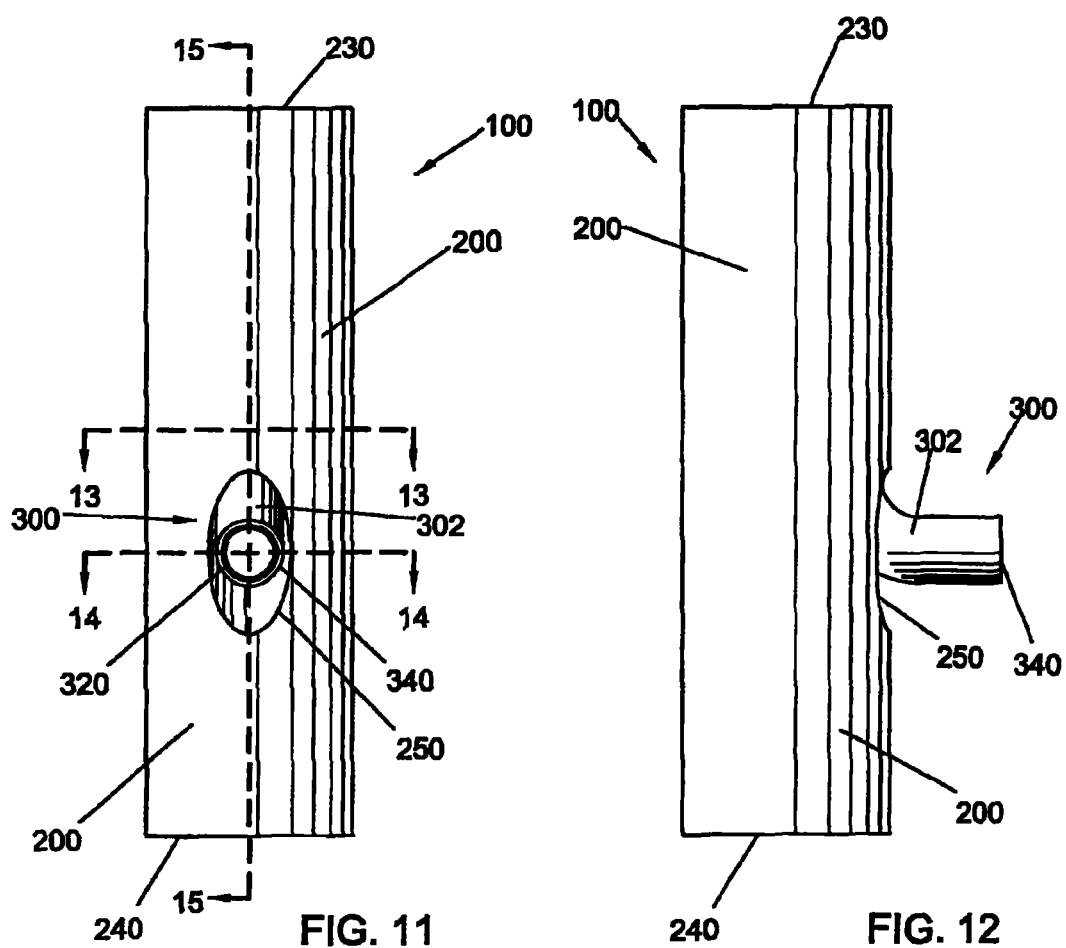
FIG. 11 shows a front view of a bifurcated stent graft according to the present invention.
FIG. 12 shows a side view of a bifurcated stent graft according to the present invention.

The embodiments shown in the Figures are exemplary, and should not be construed as limiting the scope of the present invention as disclosed and/or claimed herein.

DETAILED DESCRIPTION OF THE INVENTION

For purposes of the present written description and/or claims, "proximal" shall denote the direction along a vessel system in which multiple smaller vessels come together to form a larger vessel, and "distal" shall denote the opposite direction, i.e., the direction in which a larger vessel divides into multiple smaller vessels. For an arterial system proximal therefore corresponds to "upstream", while distal corresponds to "downstream". It should be noted that for a venous system or a lymphatic system, the correspondence would be reversed. The correspondence may vary for other vascular or duct systems.

A bifurcated intravascular primary stent graft 100 according to the present invention is illustrated in FIGS. 1-9 and comprises: a first primary stent segment 210; a second primary stent segment 220; a primary graft sleeve 200 having first open end 230, having a second open end 240, forming a main fluid flow channel 235 therebetween, and having a side opening 250 therethrough; and an internal graft channel 260 formed by partition 280 within the primary graft sleeve 200 and having an inner open end 270 within the primary graft sleeve 200 and an outer open end communicating with the side opening 250 of the primary graft sleeve 200. An internal stent segment 290 may be provided near the inner open end 270 of internal graft channel 260, to keep internal graft channel 260 open and to facilitate later deployment of a secondary stent graft (described herein below). The internal graft channel 260 and partition 280 thereby form at least a portion of a branch fluid flow channel between main channel 235 and the side opening 250 of the primary graft sleeve 200. Primary graft sleeve 200 may be operatively coupled near the first open end 230 to the first primary stent segment 210 and operatively coupled near the second open end 240 to the second primary stent segment 220, so that stent segments 210 and 220 and graft sleeve 200 thereby form a single operative unit. Each stent segment and the corresponding open end may preferably be adapted for engaging an endoluminal surface of a main vessel and forming a substantially fluid-tight seal therewith.

A bifurcated intravascular stent graft according to the present invention may comprise a primary stent graft 100 and may further comprise a secondary stent graft 300 as illustrated in FIGS. 10-15. The secondary stent graft 300 comprises: a first secondary stent segment 310; a second secondary stent segment 320; and a secondary graft sleeve 302. Secondary graft sleeve 302 may be operatively coupled near first open end 330 to the first secondary stent segment 310 and operatively coupled near second open end 340 to the second secondary stent segment 320, so that stent segments 310 and 320 and secondary graft sleeve 302 thereby form a single operative unit. Secondary stent 300 may be adapted to pass within internal graft channel 260 and through side opening 250. First stent segment 310 and corresponding first open end 330 may preferably be adapted for engaging an inner surface of internal graft channel 260 and forming a substantially fluid-tight seal therewith. Second stent segment 320 and corresponding second open end 340 may preferably be adapted for engaging an endoluminal surface of a branch vessel and forming a substantially fluid-tight seal therewith. Secondary stent graft 300 may therefore form at least a portion of the branch fluid flow channel.

The stent graft of the present invention is particularly well-suited for repair of main vessel segments where a branch vessel leaves the main vessel at an angle approaching 90°. Previous bifurcated stent graft devices enable repairs where a branch vessel leaves the main vessel at a substantially smaller angle of less than about 45°. This condition does not obtain at several potentially important vessel repair sites. Other previous devices enable repair at such high-angled branches only when transluminal access to a distal portion of the branch vessel is possible. In many instances such access is either impossible (celiac artery, mesenteric arteries, renal arteries) or extremely difficult and/or dangerous (carotid arteries). Still other previous devices do not provide a substantially fluid-tight seal with the branch vessel, thereby partially defeating the purpose of the stent graft (i.e., shielding the repaired portion of the main vessel and/or branch vessel from intravascular fluid pressure).

Figure 16:
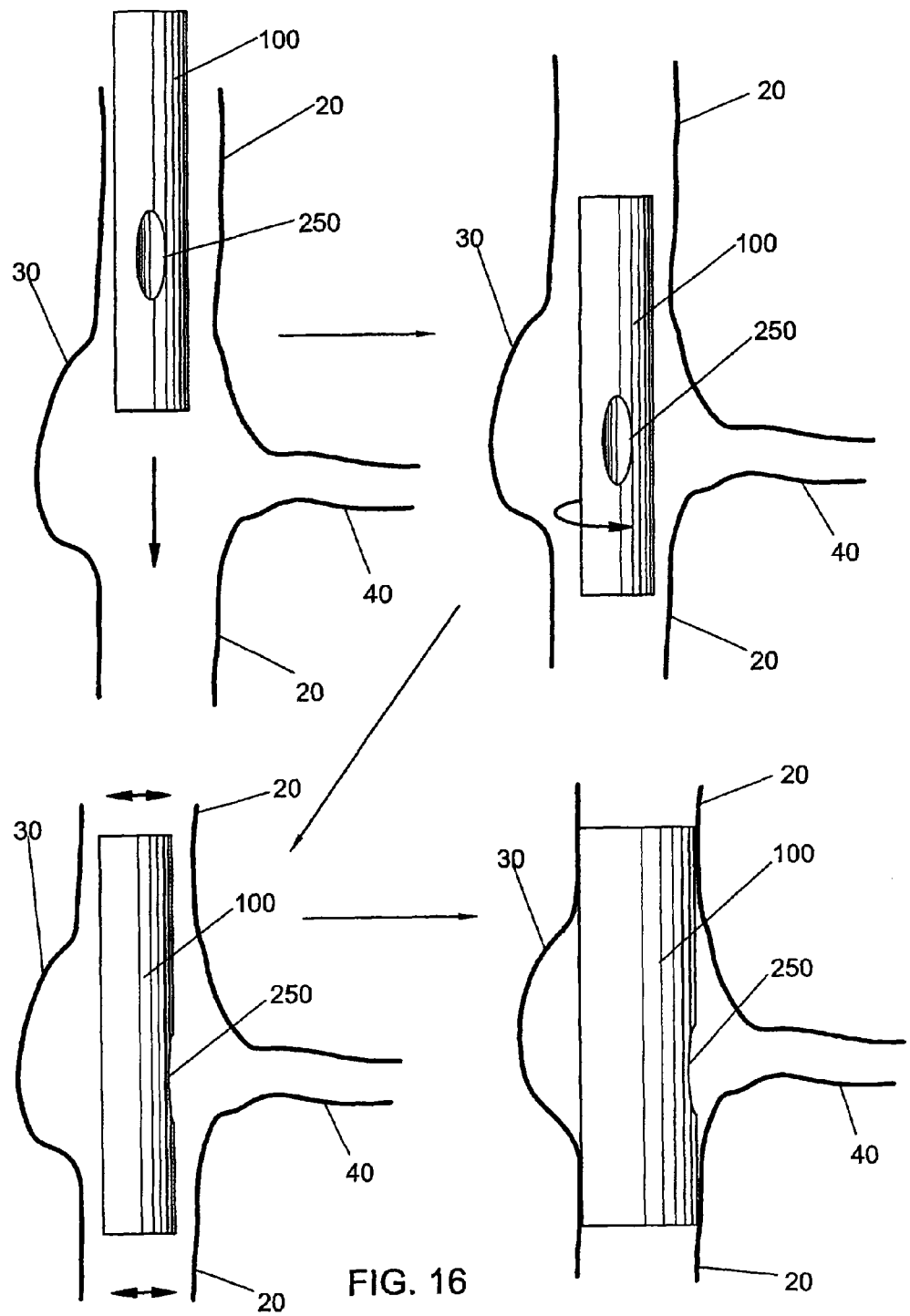
FIG. 16 shows a procedure for deploying a primary stent graft according to the present invention.

The stent graft of the present invention, in contrast, addresses these issues. As shown in FIG. 16, bifurcated primary stent graft 100 may be delivered transluminally to a repair site 30 of a main vessel 20, and may be adjusted longitudinally and/or rotated about its long axis within the main vessel lumen until side opening 250 is substantially aligned with the lumen of branch vessel 40. Bifurcated primary stent graft 100 may be provided with one or more radiopaque markers or indexes to facilitate the alignment under fluoroscopic imaging. First primary stent segment 210 and first open end 230 may be engaged with the endoluminal surface of a first segment of the main vessel 20 near the repair site to form a substantially fluid-tight seal, and second primary stent segment 220 and second open end 240 may be engaged with the endoluminal surface of a second segment of the main vessel 20 near the repair site to form a substantially fluid-tight seal, thereby deploying bifurcated primary stent graft 100 within the repair site 30 of main vessel 20. Bifurcated primary stent graft 100 may be delivered through the main vessel from upstream or from downstream, as dictated by the particular clinical circumstances.

Figure 17:
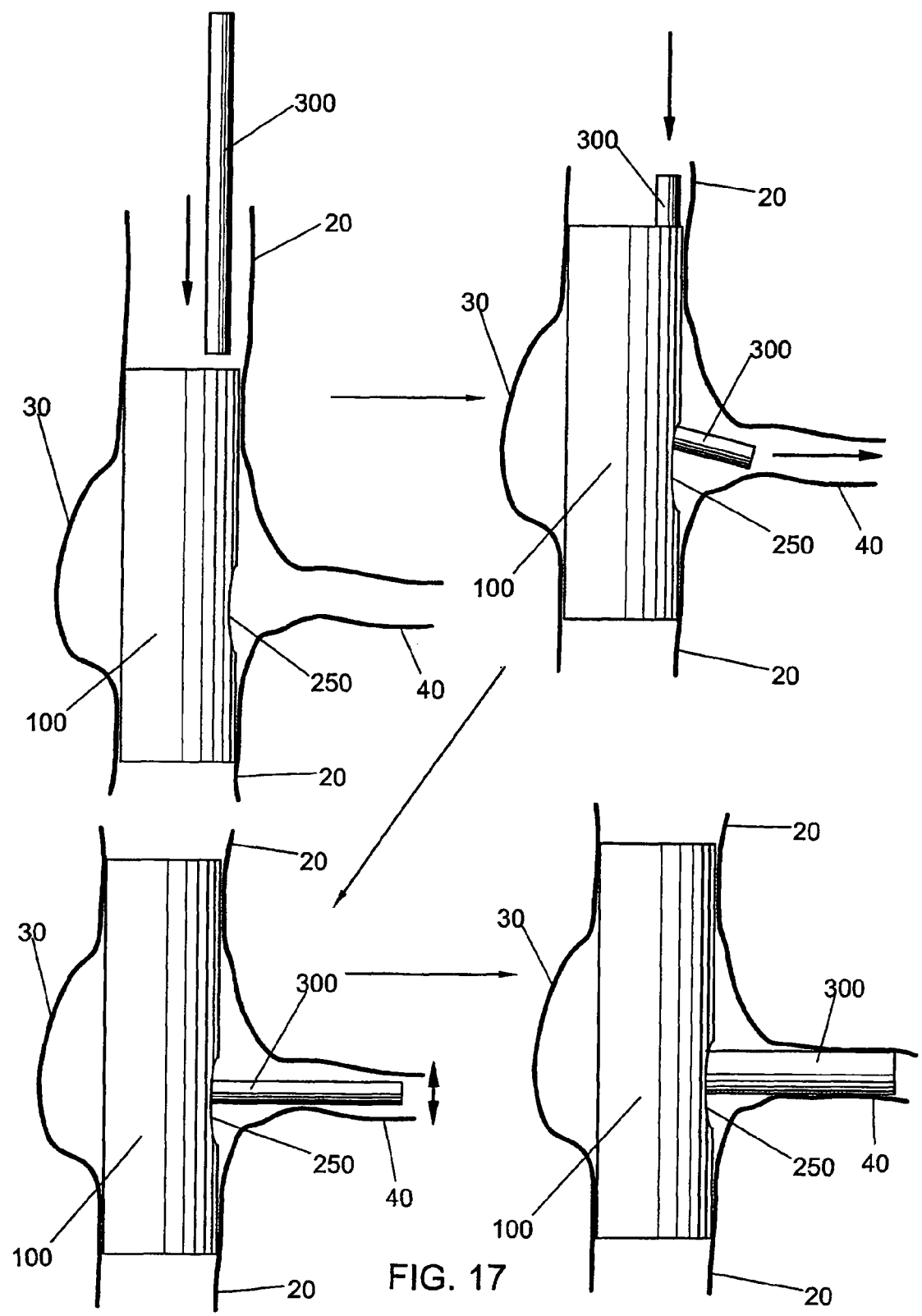
FIG. 17 shows a procedure for deploying a secondary stent graft according to the present invention.
Figure 19:
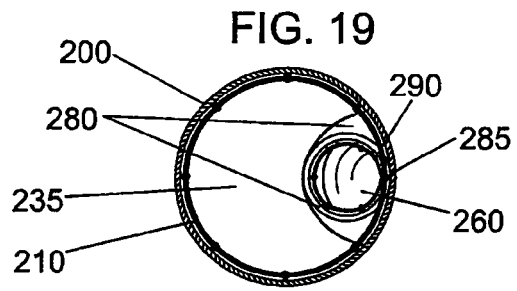
FIG. 19 shows a transverse-sectional view of a primary stent graft according to the present invention.
Figure 21:
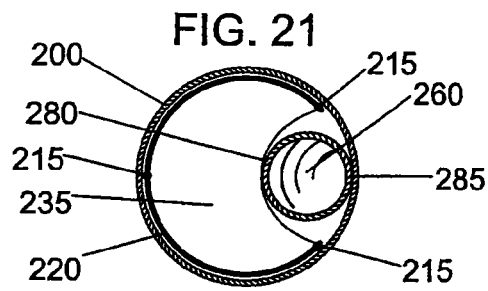
FIG. 21 shows a transverse-sectional view of a primary stent graft according to the present invention.
Figure 20:
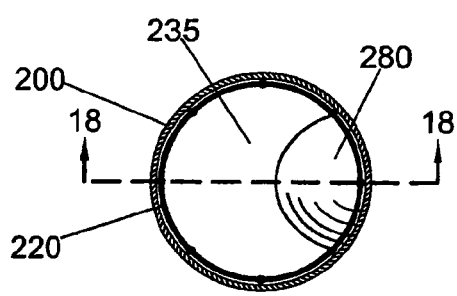
FIG. 20 shows a transverse-sectional view of a primary stent graft according to the present invention.
Figure 22:
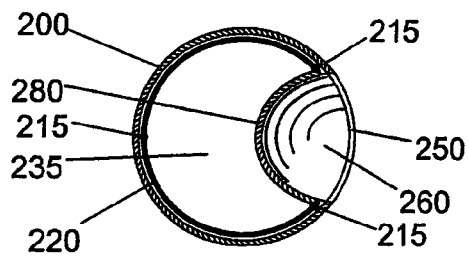
FIG. 22 shows a transverse-sectional view of a primary stent graft according to the present invention.
Figure 18:
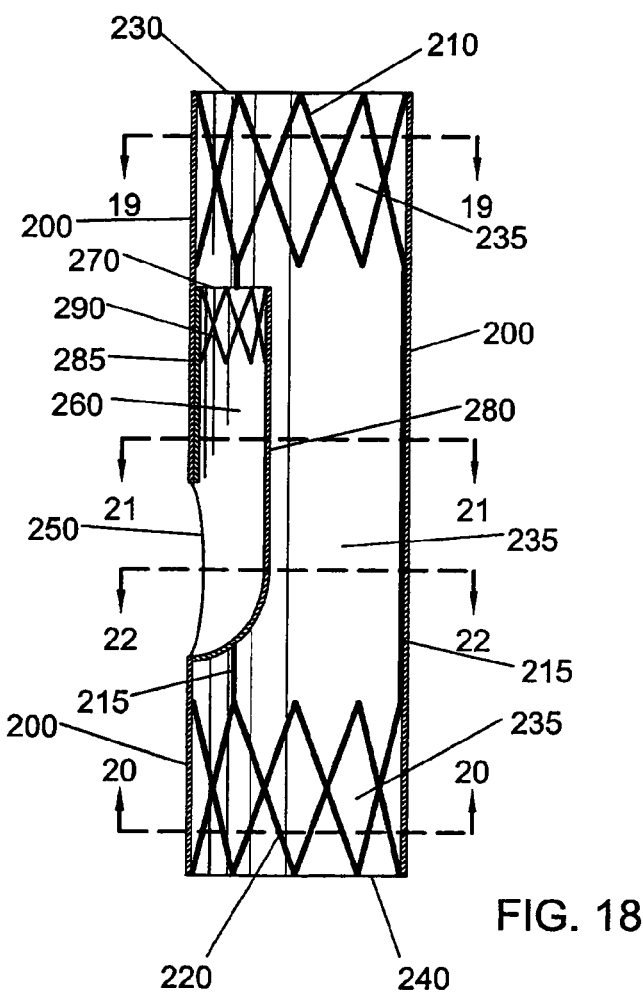
FIG. 18 shows a longitudinal-sectional view of a primary stent graft according to the present invention.

After delivery and deployment of bifurcated primary stent graft 100 at the repair site 30, secondary stent graft 300 is then delivered to the repair site and deployed, as illustrated in FIG. 17. Secondary stent graft 300 is delivered transluminally to the repair site and passed within internal graft channel 260 of primary stent graft 100. Secondary stent graft 300 may be delivered within the main vessel to the repair site from the same direction as primary stent graft 100, or from the opposite direction if feasible and/or desirable. Delivery from the same direction as delivery of primary stent graft 100 within the main vessel may be preferred due to the preferred construction of internal graft channel 260. Secondary stent graft 300 may also be delivered from a distal point within the branch vessel 40 if feasible and/or desirable. Secondary stent graft 300 is positioned at least partially within internal graft channel 260, passing through side opening 250 and into branch vessel 40. Secondary stent graft 300 may be provided with one or more radiopaque markers or indexes to facilitate the positioning under fluoroscopic imaging. First secondary stent segment 310 and first open end 330 may be engaged with the inner surface of the internal graft channel 260 to form a substantially fluid-tight seal, and second secondary stent segment 320 and second open end 340 may be engaged with the endoluminal surface of the branch vessel 40 to form a substantially fluid-tight seal, thereby deploying secondary stent graft 300 within the internal graft channel 260 and the branch vessel 40. When deployed together in this way, the first and second substantially fluid-tight seals of primary stent graft 100 and secondary stent graft 300 together substantially shield the main vessel walls and/or the branch vessel walls at the repair site from intravascular fluid pressure, while preserving fluid flow both through the main vessel and into the branch vessel.

Once deployed, incoming fluid flow (i.e., arterial or venous blood flow in the typical deployment scenario) may enter either open end 230 or 240 of bifurcated stent graft 100 and pass through main fluid flow channel 235. Upon reaching the inner open end 270 of internal graft channel 260, the incoming fluid flow divides into a portion continuing to flow in the main fluid flow channel 235 and a portion flowing through the branch fluid flow channel within internal graft channel 260 and through side opening 250. The fluid flow in main channel 235 continues out of bifurcated stent graft 100 and back into the main vessel 20. The branch fluid flow channel comprises a portion of internal graft channel 260 and the interior of secondary stent graft 300, and the branch fluid flow passes into the open inner end 270 of internal graft channel 260, into the open first end 330 of secondary stent graft 300, through secondary stent graft 300 (and therefore through side opening 250), out of open second end 340 of secondary stent graft 300, and into branch vessel 40. Stent graft 300 may preferably be made sufficiently flexible to be bent through angles ranging from about 0° through about 180° while still forming a portion of the branch fluid flow channel. In this way the bifurcated stent graft of the present invention may be used to repair main vessels near where branch vessels leave the main vessel at arbitrarily large angles, even approaching about 180°. To facilitate longitudinal and/or rotational alignment of bifurcated primary stent graft 100 relative to the lumen of the branch vessel, side opening 250 through primary graft sleeve 200 may be made substantially larger than the lumen, thereby increasing the range of positions of bifurcated primary stent graft 100 that nevertheless enable passing secondary stent graft 300 through side opening 250 and into branch vessel 40. It may be desirable for internal graft channel 260 to increase in size with distance from inner open end 270, so that the size of the open inner end of internal graft channel 260 may substantially match the size of secondary stent graft 300 and/or the lumen of branch vessel 40, while the outer open end of internal graft channel 260 may substantially match the relatively enlarged size of side opening 250.

Without departing from inventive concepts disclosed and/or claimed herein, any suitable configuration and/or materials (currently known or hereafter developed) may be employed for stent segments 210, 220, 290, 310, and/or 320. Many suitable configurations for intravascular stents have been developed over the years, as disclosed in the incorporated references and in references cited therein (U.S. Pat. Nos. 5,855,598 and 6,093,203 are of particular note for containing many examples). Such stent configurations may include but are not limited to braids (open-lattice or closely-woven), helical structural strands, sinusoidal structural strands, mesh-like materials, diamond-shaped mesh, rectangular shaped mesh, functional equivalents thereof, and/or combinations thereof. Materials should be sufficiently strong, bio-compatible, hemo9 compatible, corrosion-resistant, and fatigue-resistant, and may include metals, plastics, stainless steels, stainless spring steels, cobalt-containing alloys, titanium-containing alloys, nitinol, nickel-containing alloys, nickel-titanium alloys, composite materials, clad composite materials, other functionally equivalent materials (extant or hereafter developed), and/or combinations thereof. Whatever its construction, a stent graft may typically be delivered transluminally to a vascular repair site with the stent segment in a radially compressed configurations having a delivery diameter sufficiently small to pass through any required vessels to the repair site. Once positioned properly, the stent segment may be radially enlarged to a deployed diameter. The stent segment may be fabricated so that the delivery diameter is achieved through elastic radial compression of the stent segment (maintained during transluminal delivery by a sleeve or equivalent device). Once properly positioned, the sleeve or equivalent device may be removed, thereby allowing the stent segment to expand to its deployed diameter. The deployed diameter may be smaller than the uncompressed diameter of the stent segment, so that residual elastic expanding force exerted by the stent segment may serve to hold the vessel open, fix the stent in place in the vessel, and/or form a substantially fluid-tight seal with the endoluminal surface of the vessel (in conjunction with a graft sleeve). Alternatively, the stent segment may comprise material(s) that undergo plastic deformation. The stent graft may be delivered transluminally with the stent segment having a delivery diameter sufficiently small to allow delivery to the repair site. The stent segment may then be expanded (by an intra-luminal balloon catheter or other functionally equivalent device) to a deployed diameter, and may maintain the deployed diameter due to plastic deformation of the stent segment during expansion. The expanded stent segment may serve to engage the endoluminal surface of the vessel to hold the vessel open, hold the stent graft in position, and/or form a substantially fluid-tight seal with the vessel. Other methods of delivery and/or deployment may be employed without departing from inventive concepts disclosed and/or claimed herein.

Whatever configuration of stent segment(s) is employed, the stent segment must be adapted to engage the endoluminal surface of the vessel. This may be accomplished by any suitable method (currently known or hereafter developed; for example as disclosed in the incorporated references and in references cited therein), including but not limited to: elastic or plastic expansion; sutures; ligatures; clips; barbs; endoluminal cellular overgrowth; functional equivalents thereof; and/or combinations thereof.

Figure 32:
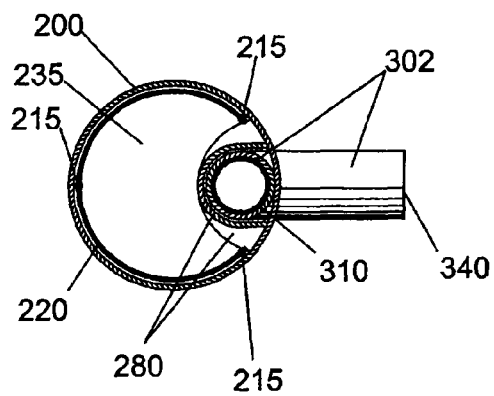
FIG. 32 shows a transverse-sectional view of a bifurcated stent graft according to the present invention.
Figure 33:
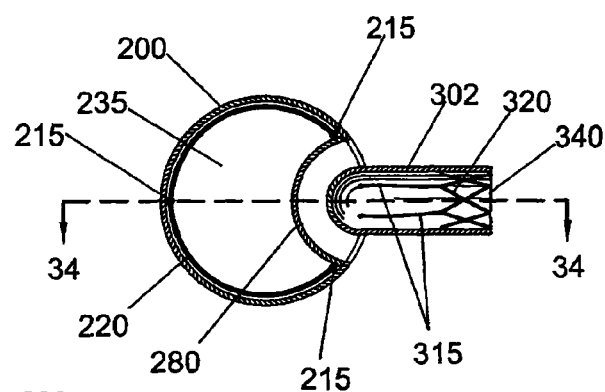
FIG. 33 shows a transverse-sectional view of a bifurcated stent graft according to the present invention.
Figure 34:
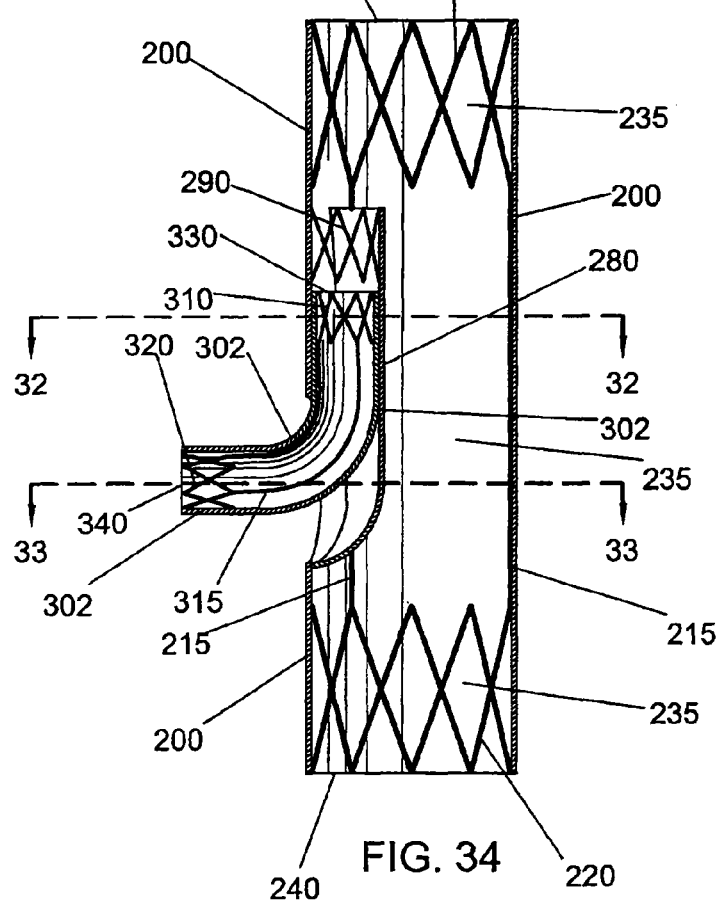
FIG. 34 shows a longitudinal-sectional view of a bifurcated stent graft according to the present invention.
Figure 35:
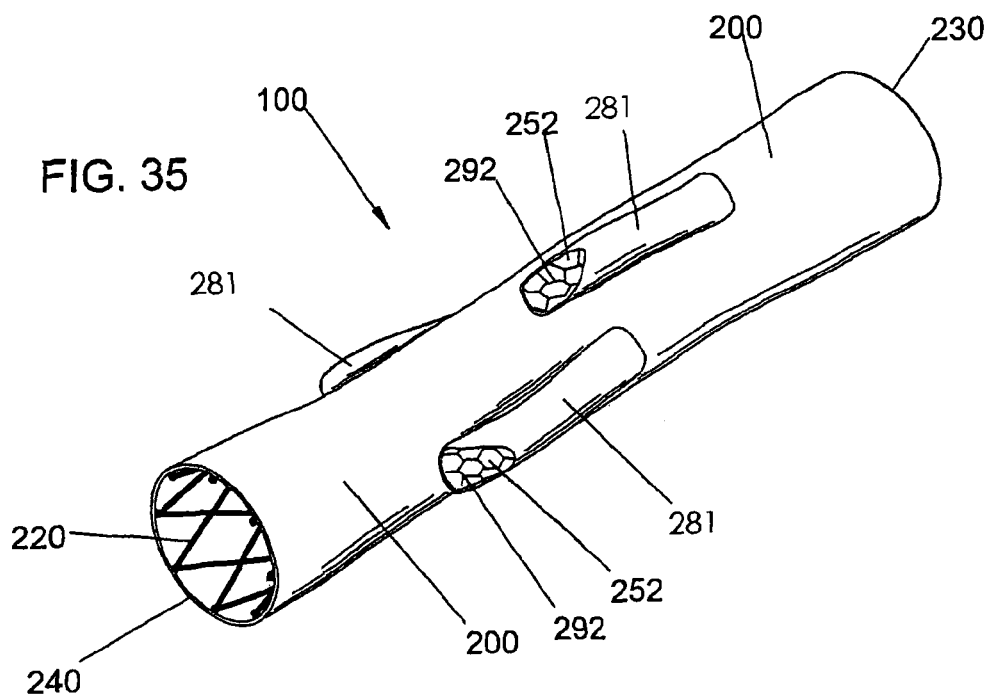
FIG. 35 shows an isometric view of a primary stent graft according to the present invention.

First and second stent segments corresponding to a single graft sleeve of a single stent graft have been shown herein as separate structural elements. Pairs of first and second stent segments (segments 210 and 220, for example, or 310 and 320) may be mechanically connected by a stent coupling member. Three longitudinal wires 215 are shown serving to connect stent segments 210 and 220 of primary stent graft 100, while longitudinal wires 315 are shown serving to connect stent segments 310 and 320 in FIGS. 32, 33, and 34. Other functionally equivalent configurations may be employed without departing from inventive concepts disclosed and/or claimed herein. In particular, it may be desirable for corresponding first and second stent segments to comprise first and second ends of a single stent. In the case of stent segments 210 and 220, a single primary stent would require an side opening corresponding to side opening 250 of graft sleeve 200. No such side opening would be required for a single secondary stent comprising first and second segments 310 and 320. Such a single stent may be preferred for secondary stent graft 300, since it is typically bent to enter a branch vessel but must nevertheless maintain an open branch fluid channel.

Without departing from inventive concepts disclosed and/or claimed herein, any suitable configuration and/or materials (currently known or hereafter developed) may be employed for primary graft sleeve 200, partition 280, and/or graft sleeve 300. Such sleeve materials may include, but are not limited to:

continuous sheets; interwoven textile strands; multiple filament yarns (twisted or un-twisted); monofilament yarns; PET (Dacron), polypropylene, polyethylene, high-density polyethylene, polyurethane, silicone, PTFE, polyolefins, ePTFE, biologically-derived membranes (such as swine intestinal submucosa), functional equivalents thereof, and/or combinations thereof. The graft sleeve may be delivered at the size appropriate for deployment at the repair site, or may be a smaller size and stretched (plastically deformed) at the repair site to the desired deployed size. Graft sleeves are shown herein outside the corresponding stent segment, but the stent segment may equivalently be outside the corresponding graft sleeve. The graft sleeve and corresponding stent segment(s) may be operatively coupled by any suitable method (currently known or hereafter developed), including but not limited to: sutures, ligatures, clips, barbs, adhesives (silicone, siloxane polymer, fluorosilicones, polycarbonate urethanes, functional equivalent thereof, and/or combinations thereof); functional equivalent thereof, and/or combinations thereof. Alternatively, a graft sleeve and corresponding stent segment(s) may comprise a single integral structure. Without departing from inventive concepts disclosed and/or claimed herein, an end of a graft sleeve and the corresponding stent segment may extend longitudinally substantially equally (as shown in the Figures), the graft sleeve may extend longitudinally beyond the stent segment, or the stent segment may extend longitudinally beyond the graft sleeve. Without departing from inventive concepts disclosed and/or claimed herein, a graft sleeve may be adapted to engage an endoluminal vessel surface by endoluminal cellular invasion (by manipulation of graft sleeve porosity or other equivalent technique), thereby substantially fixing the graft sleeve to the vessel and forming a substantially fluid-tight seal therewith.

In the present invention, a substantially fluid-tight seal between a stent graft and a vessel may be achieved by adapting the graft sleeve and corresponding stent segment to engage the endoluminal surface of the vessel. This may be readily achieved by using a graft sleeve outside the stent segment. Expansion of the stent segment (either elastic or plastic) may then serve to press the graft sleeve against the inner vessel surface, thereby forming the substantially fluid-tight seal. For a graft sleeve inside the stent segment, a substantially fluid-tight connection between the stent segment and the graft sleeve is required, thereby resulting in a substantially fluid-tight seal between the graft sleeve and vessel surface when the stent segment engages the vessel surface. Without departing from inventive concepts disclosed and/or claimed herein, many other functionally equivalent configurations (currently known or hereafter developed) may be contrived for operatively coupling a graft sleeve to a stent segment, and for engaging an endoluminal surface of the vessel and forming a substantially fluid-tight seal therewith.

Internal graft channel 260 and partition 280 may be formed in a variety of functionally equivalent ways without departing from inventive concepts disclosed and/or claimed herein. As shown in FIGS. 1-15, internal graft channel 260 may be formed by securing an elongated sheet of graft sleeve material to the inner surface of graft sleeve 200 with substantially fluid-tight seams along each side edge of the sheet and along one end of the sheet, with the sheet serving as partition 280. Alternatively, an internal graft sleeve having open inner and outer ends may be secured longitudinally to the inner surface of graft sleeve 200 (FIGS. 18-22). The internal graft sleeve may be secured along one or more longitudinal seams 285, and/or at one or more discrete contact points. The open inner end 270 of the internal sleeve may preferably be secured to the inner surface of graft sleeve 200 while remaining open, thereby facilitating subsequent insertion of secondary stent graft 300 thereinto. The sides of the internal graft sleeve serve as partition 280. The outer open end of the internal graft sleeve may be secured around its perimeter to side opening 250 of graft sleeve 200 to form a substantially fluid-tight seal. The outer end of the internal graft sleeve may be adapted to facilitate communicating with and securing to side opening 250 in a variety of ways, including but not limited to: enlarging the outer end of the internal graft sleeve (FIG. 23); providing the outer end with a diagonal opening (FIGS. 23 and 24); providing the internal graft sleeve with a side opening 284 near the outer end thereof (the outer end itself would then preferably be closed; FIG. 25); functionally equivalent methods; and/or combinations thereof. Seams and/or contact points for securing two graft sleeves together and/or securing a sheet of graft sleeve material to a graft sleeve and may be accomplished by any suitable technique (extant or hereafter developed), including but not limited to: sutures, ligatures, clips, other fasteners, fusion bonding, electronic welding, thermal bonding, thermal welding, chemical welding, adhesives, functional equivalents thereof, and/or combinations thereof.

FIGS. 26-31 illustrate an embodiment of primary stent graft 100 in which the internal primary graft channel 260 is formed by securing together, along a substantially longitudinal seam 282, portions of an inner surface of the primary graft sleeve 200 separated by a circumferential seam spacing. The first end of the seam 282 extends toward the first end 230 of the primary graft sleeve 200 beyond the side opening 250, while the second end of the seam 282 extends toward the second end 240 of the primary graft sleeve 200 beyond the side opening 250. The circumferential seam spacing decreases to substantially zero at the second end of the seam, and the side opening 250 lies within the circumferential seam spacing. In this way a single graft sleeve 200 may be used to provide both main and branch fluid flow channels, thereby simplifying manufacture of the bifurcated stent graft. Secondary stent graft 300 may be inserted through internal primary graft channel 260, out through side opening 250, and into the branch vessel in substantially the same manner as described hereinabove.

FIGS. 35-41 illustrate an embodiment of a bifurcated stent graft in which multiple side openings 250 are provided in the primary graft sleeve 200, each as a circumferential slit in the graft sleeve. A portion of the graft sleeve adjacent the slit is pushed inward, producing an opening. An external primary graft channel 252 is formed by securing (by suturing, thermal bonding, or other suitable techniques) additional graft material to the outer surface of the primary graft sleeve 200. The additional graft material may take the form of a sleeve 281 secured to the exterior of the primary graft sleeve 200 (as shown in FIGS. 35-41), or may be provided by securing a strip of graft material along its side edges to the exterior of the primary graft sleeve 200, forming the external primary graft channel 252 between the strip and the primary graft sleeve 200. In either case, the external graft channel 252 thus formed communicates with interior of the primary graft sleeve 200 (i.e., with the primary graft channel 235) through the opening 250 in the primary graft sleeve 200, and provides a fluid flow channel 262 between the primary graft channel 235 through the primary graft sleeve 200. Three such external primary graft channels 252 are shown in the Figures at varying longitudinal and circumferential positions. This exemplary arrangement might be suitable for a stent graft in the abdominal aorta spanning the branch points of the renal arteries and superior mesenteric arteries, for example. Other numbers and/or arrangements of the external primary graft channels may be employed that may be suitable for other stent graft locations while remaining within the scope of the present invention. This embodiment may be more readily fabricated than others since all seams may be made on the exterior surface of the primary graft sleeve.

Figure 36:
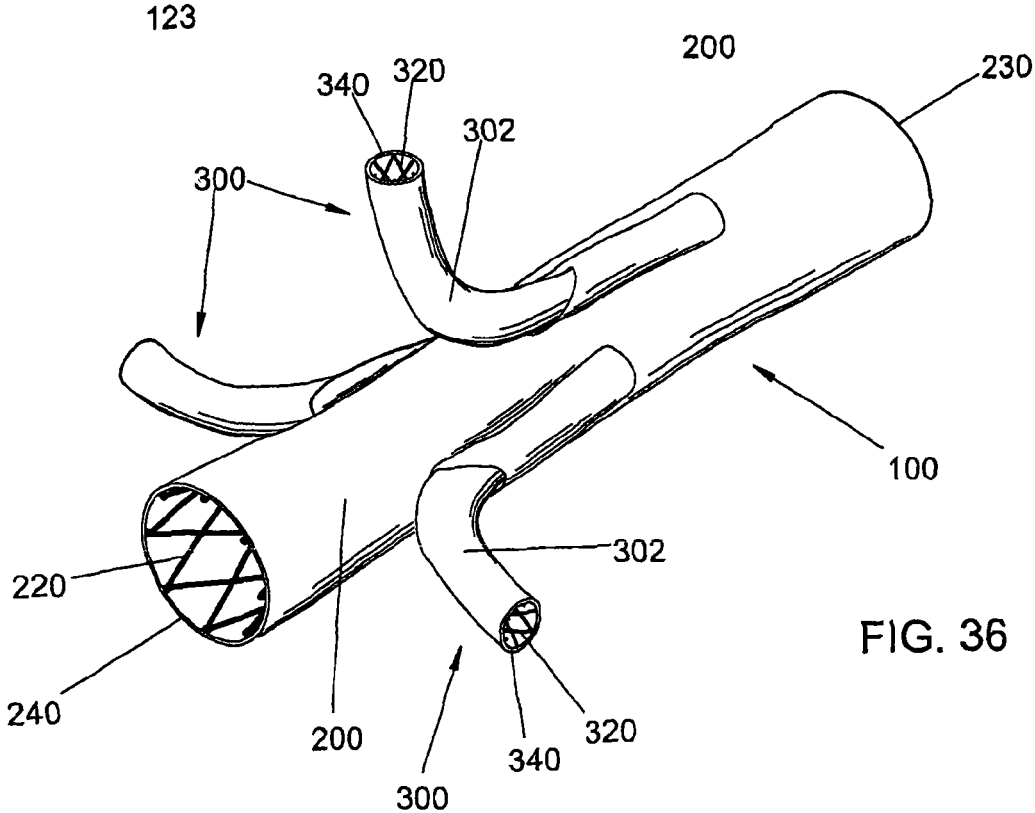
FIG. 36 shows an isometric view of a bifurcated stent graft according to the present invention.
Figure 37:
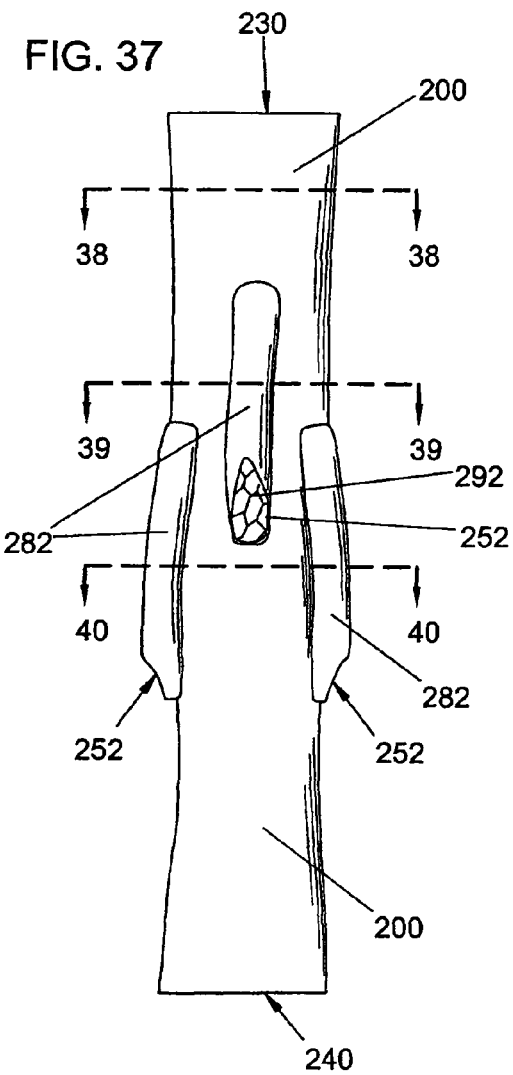
FIG. 37 shows a front view of a primary stent graft according to the present invention.
Figure 41:
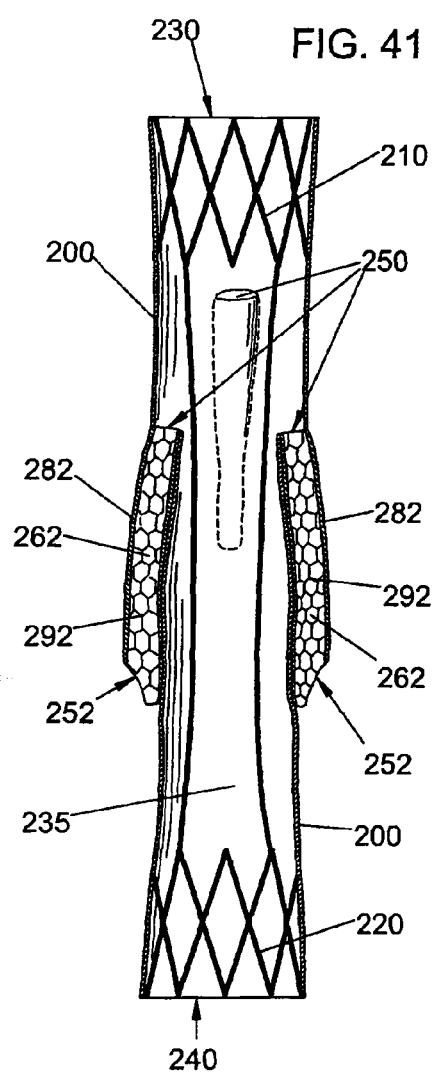
FIG. 41 shows a longitudinal-sectional view of a primary stent graft according to the present invention.
Figure 38:
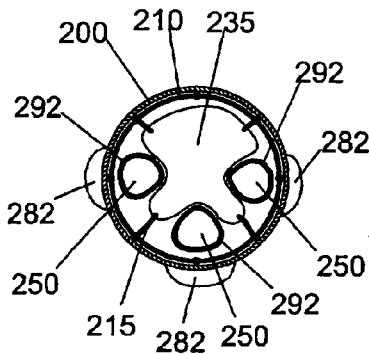
FIG. 38 shows a transverse-sectional view of a primary stent graft according to the present invention.
Figures 39, 40:
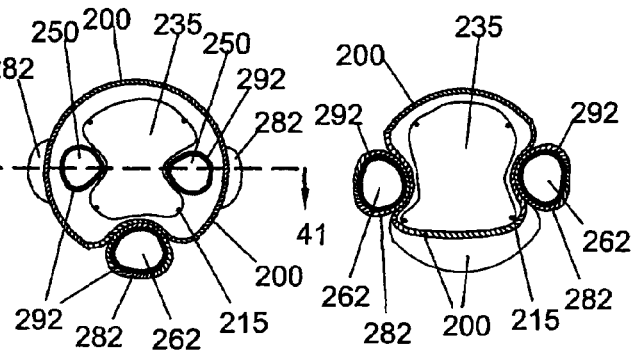
FIG. 39 shows a transverse-sectional view of a primary stent graft according to the present invention.
FIG. 40 shows a transverse-sectional view of a primary stent graft according to the present invention.

The primary graft sleeve 200 shown in FIGS. 35-41 may be provided with stent segments 210/220 near the ends 230/240 thereof and with stent coupling members 215 as disclosed hereinabove. Each external primary graft channel 262 is shown with a stent segment 292 for providing structural support and for keeping the opening 250 through the primary graft sleeve 200 open. A hexagonal wire mesh extending along substantially the entire length of the external primary graft channel is shown, but other stent configurations may be equivalently employed (including separate first and second stent segments positioned within the external primary graft channel near the ends thereof [with or without a stent coupling member], a single stent segment within the external primary graft channel near the primary graft sleeve opening, or other suitable arrangements). In FIG. 36, the primary stent graft 100 is shown with a secondary stent graft 300 positioned in and extending from each of the external primary graft channels 262. The secondary stent grafts 300 may preferably include a secondary graft sleeve 302 and secondary stent segments 310/320 within the secondary graft sleeve 302 near the ends thereof. The stent segments 310/320 may be separate (as in FIG. 15), may be connected by stent segment coupling members 315 (as in FIG. 34), or may comprise the ends of a single stent extending substantially the entire length of the secondary graft sleeve 302 (not shown). When deployed (as in FIG. 16), the primary stent graft 100 of FIG. 35 may form substantially fluid-tight seals with an endoluminal surface of a vessel near the ends of the primary stent graft, by engagement of the stent segments 210/220 with the vessel. The primary stent graft 100 may therefore span a damaged portion of the vessel (including any branch points). The side opening(s) 250 and external primary graft channel(s) 262 therefore communicate with a fluid volume that is substantially isolated from intravascular volumes both upstream and downstream of the primary stent graft. One or more secondary stent grafts 300 may be deployed through corresponding side opening(s) 250, into corresponding external primary graft channel(s) 262, and into corresponding branch vessel(s) (as in FIG. 17). The proximal end 330 of a secondary stent graft 300 thus deployed forms a substantially fluid-tight seal within the corresponding external primary graft channel 262, while the distal end 340 forms a substantially fluid-tight seal within the branch vessel. A blood flow channel is thereby provided from the primary graft channel 235 into the branch vessel, while substantially isolating the damaged portion of the vessel (including the branch point) from intravascular fluid pressure.

The present invention has been set forth in the forms of its preferred and alternative embodiments. It is nevertheless intended that modifications to the disclosed bifurcated intravascular stent graft and methods for deploying the same may be made without departing from inventive concepts disclosed and/or claimed herein.

What is claimed is:

1. A method for deploying an intravascular stent graft comprising the steps of:

providing an intravascular stent graft comprising first and second primary stent segments; a primary graft sleeve operatively coupled near an open first end thereof to the first primary stent segment, operatively coupled near an open second end thereof to the second primary stent segment, having a side opening therethrough, and forming a main fluid flow channel between the open first and second ends of the primary graft sleeve; and a strip of graft material having opposite side edges that are fixedly secured to an outer surface of the primary graft sleeve to form an external graft channel between the strip graft material and the primary graft sleeve, the external graft channel having a first open end secured to and communicating with the side opening of the primary graft sleeve and a second open end extending toward the second end of the primary graft sleeve and secured to the exterior surface of the primary graft sleeve, thereby forming at least a portion of a branch fluid flow channel between the main fluid flow channel and the second open end of the external graft channel, wherein the external graft channel further includes at least one stent segment at or near the side opening of the intravascular stent graft;

delivering transluminally the intravascular stent graft to a repair site of the main vessel;

locating the intravascular stent graft to substantially align the second open end of the external graft channel with a lumen of a branch vessel of the main vessel at the repair site;

engaging the first primary stent segment and the first end of the primary graft sleeve with the endoluminal surface of the first segment of the main vessel; and engaging the second primary stent segment and the second end of the primary graft sleeve with the endoluminal surface of the second segment of the main vessel.

2. The method of claim 1, further comprising the steps of:

compressing radially at least one of the first primary stent segment, the second primary stent segment, and the primary graft sleeve to a respective delivery diameter for delivering transluminally the stent graft to the repair site of the main vessel; and expanding radially at least one of the first primary stent segment, the second primary stent segment, and the primary graft sleeve to a respective deployed diameter for engaging the endoluminal surface of the main vessel.

3. The method of claim 2, further comprising the steps of:

providing a secondary stent graft; and passing the secondary stent graft through the side opening of the primary graft sleeve, into the external graft channel, and into the branch vessel.

4. The method of claim 1, wherein the second open end of the external graft channel is beveled and longitudinally spaced apart from the side opening, thereby enabling the secondary stent graft to form at least a portion of the branch fluid flow channel and accommodating bending of the secondary stent graft to form an angle ranging from about 0° up to about 180° with the primary stent graft.

5. The method of claim 3, further comprising the step of bending the secondary stent graft through an angle ranging from about 0° up to about 180° for passing the secondary stent graft into the branch vessel and forming at least a portion of the branch fluid flow channel.

* * * * *